United States Patent
Kasai et al.

(10) Patent No.: US 6,406,904 B1
(45) Date of Patent: Jun. 18, 2002

(54) PROCESS FOR PREPARING OPTICALLY ACTIVE 4-HALOGENO-1,3-BUTANEDIOL AND ITS DERIVATIVE USING PSEUDOMONAS

(75) Inventors: Naoya Kasai, Sennan-gun; Toshio Suzuki, Osaka; Hideaki Idogaki, Osaka; Atsushi Nakagawa, Osaka, all of (JP)

(73) Assignee: Daiso Co., Ltd., Osaka-fu (JP)

( * ) Notice: Subject to any disclaimer, the term of this patent is extended or adjusted under 35 U.S.C. 154(b) by 0 days.

(21) Appl. No.: 09/695,870

(22) Filed: Oct. 26, 2000

(30) Foreign Application Priority Data

Oct. 26, 1999 (JP) ............................................ 11-303817

(51) Int. Cl.⁷ .......................... C12P 41/00; C12P 17/04; C12P 7/18
(52) U.S. Cl. ........................ 435/280; 435/158; 435/126
(58) Field of Search ................................ 435/280, 158, 435/126

(56) References Cited

FOREIGN PATENT DOCUMENTS

| EP | 0434393 | 6/1991 |
| EP | 0745681 | 12/1996 |
| JP | 06209781 A | 8/1994 |
| JP | 09047296 A | 2/1997 |

OTHER PUBLICATIONS

Database WPI, Section Ch, Week 198718 Derwent Publications Ltd., London, GB; Class B05, AN 1987–126930 XP002159211 & JP 62 069993 A (Osaka Soda KK), Mar. 31, 1987.

Suzuki et al., "A Novel Generation of Optically Active Ethyl 4–Chloro–3–hydroxybutyrate as a C4 Chiral Building Unit Using Dechlorination", Tetrahedron: Asymmetry, vol. 7, No. 11, Nov. 8, 1996, pp. 3109–3112.

Suzuki et al., "Dual production of highly pure methyl (R)–4–chloro–3–hydroxybutyrate and (S)–3–hydroxy–γ–butyrolactone with *Enterobacter sp.*", Enzyme Mcrob. Technol., vol. 24, Jan./Feb. 1, pp. 13–20.

*Primary Examiner*—Sandra E. Saucier
(74) *Attorney, Agent, or Firm*—Wenderoth, Lind & Ponack, L.L.P.

(57) ABSTRACT

A process for preparing an optically active 4-halogeno-1,3-butanediol and (R)-1,2,4-butanetriol or (S)-3-hydroxy-γ-butyrolactone which comprises reacting a racemic 4-halogeno-1,3-butanediol with a specific microorganism belonging to the genus Pseudomonas.

12 Claims, No Drawings

PROCESS FOR PREPARING OPTICALLY ACTIVE 4-HALOGENO-1,3-BUTANEDIOL AND ITS DERIVATIVE USING PSEUDOMONAS

TECHNICAL FIELD

The present invention relates to biochemically preparing methods of a C4 optically active compound, namely an optically active 4-halogeno-1,3-butanediol, and its derivatives, namely an optically active 1,2,4-butanetriol and an optically active 3-hydroxy-γ-butyrolactone, which are very important as intermediates in making optically active compounds, such as pharmaceuticals, agrochemicals or physiologically active compounds.

PRIOR ART

1) As to a process for preparing an optically active 4-halogeno-1,3-butanediol, there is known a process for preparing it by reducing an optically active 4-halogeno-3-hydroxybutanoic acid ester with sodium boron hydrate or calcium boron hydrate (Japanese Patent Publication A 2-174733, Japanese Patent Publication A 9-77759 and Japanese Patent Publication B 7-76209).

2) As to a biochemically preparing method of an optically active 1,2,4-butanetriol, Nikaido et al. reported a process of it by reacting racemic 1,2,4-butanetriol with a microorganism belonging to the genus Pseudomonas to degrade (S)-1,2,4-butanetriol and by recovering (R)-1,2,4-butanetriol from the residual (Japanese Patent Publication A 6-209781). However, according to this method only (R)-1,2,4-butanetriol is obtainable, but (S)-1,2,4-butanetriol is not obtainable.

3) As to a biologically preparing method of an optically active 3-hydroxy-γ-butyrolactone, there is a known process for preparing it by reacting resting cells of a microorganism with a racemic 4-chloro-3-hydroxybutanoic acid ester (Japanese Patent Publication A 9-47296, and Enzyme Microb. Technol., 24, 13–20(1999)).

4) A biochemical resolution of chlorohydrin and its derivatives was disclosed in Japanese Patent Publication A 9-47296, but there is no concrete description on the use of a 4-halogeno-1,3-butanediol as a substrate. Furthermore, there is neither description on the biochmical conversion from an optically active 4-halogeno-1,3-butanediol to an optically active 1,2,4-butanetriol or an optically active 3-hydroxy-γ-butyrolactone.

5) There has been no report on the conversion into an optically active 1,2,4-butanetriol or an optically active 3-hydroxy-γ-butyrolactone by using an optically active 4-chloro-1,3-butanediol as a substrate. As a matter of course, any example using biological catalyst such as a microorganism in that conversion has not been reported.

DETAILED DESCRIPTION OF THE INVENTION

An optically active 4-halogeno-1,3-butanediol, an optically active 1,2,4-butanetriol and an optically active 3-hydroxy-γ-butyrolactone are very important as intermediates in making pharmaceuticals, agrochemicals or physiologically active compounds and therefore, more economical and more convenient processes for preparing them have been desired.

The present inventors extensively engaged in study for solving the above problems and completed the present invention.

The present invention relates to a process for preparing an optically active 4-halogeno-1,3-butanediol represented by the formula [1]

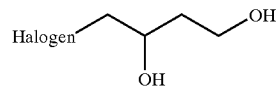

and (R)-1,2,4-butanetriol represented by the formula [2]

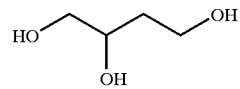

or (S)-3-hydroxy-γ-butyrolactone represented by the formula [3]

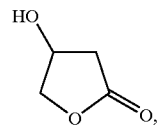

which comprises reacting a racemic 4-halogeno-1,3-butanediol represented by the formula [1] with a microorganism, its culture broth or an enzyme(s) derived from said microorganism to prepare the optically active compound[1] and the compound[2] in (R)-form or the compound[3] in (S)-form.

That is, the method of the present invention comprises reacting a racemic 4-halogeno-1,3-butanediol[1] with a specific microorganism belonging to the genus Pseudomonas, its culture broth or an enzyme(s) derived from said microorganism to cause to stereoselective dehalogenation of a (R)-4-halogeno-1,3-butanediol[1], and by kinetic resolution obtaining a (S)-4-halogeno-1,3-butanediol[1] remained in the reaction solution and (R)-1,2,4-butanetriol[2] formed (abbreviated as (R)-form[2]), or reacting a racemic 4-halogeno-1,3-butanediol[1] (abbreviated as racemate[1]) with a specific microorganism belonging to the genus Pseudomonas, its culture broth or an enzyme(s) derived from said microorganism to cause to stereoselective dehalogenation of a (S)-4-halogeno-1,3-butanediol[1] (abbreviated as (S)-form[1]), and by kinetic resolution obtaining a (R)-4-halogeno-1,3-butanediol[1] (abbreviated as (R)-form[1]) remained in the reaction solution and (S)-3-hydroxy-γ-butyrolactone[3] (abbreviated as (R)-form[3]) produced.

More in detail, the present invention relates to (i) a process for preparing (S)-form [1] and/or (R)-form [2] by reacting racemate [1] with Pseudomonas sp. DS-K-436-1, its culture broth or an enzyme(s) derived from said strain to prepare (S)-form [1] and (R)-form [2] and then isolating the resulting (S)-form [1] and/or (R)-form [2], and (ii) a process for preparing (R)-form [1] and/or (S)-form [3] by reacting racemate [1] with Pseudomonas sp. DS-SI-5, its culture broth or an enzyme(s) derived from said strain to prepare (R)-form [1] and (S)-form [3] and then isolating the resulting (R)-form [1] and/or (S)-form [3].

The present invention relates to, also a process for converting an optically active compound[1] into an optically active compound[2] or an optically active compound[3] with a microorganism belonging to the genus Pseudomonas or its culture broth or an enzyme(s) derived from said microorganism without any substantial racemization.

More in detail, the present invention relates to a process for an optically active compound[2] by reacting an optically active compound[1] with Psedomonas sp. DS-K-436-1, Psedomonas sp. OS-K-29, its culture broth, or an enzyme(s) derived from the strain,
and a process for preparing an optically active compound[3] by reacting an optically active [1] with Psedomonas sp. DS-SI-5, its culture broth, or an enzyme(s) derived from the strain.

As mentioned above, according to the present invention, there can be economically and conveniently obtainable a C4 optically active compound, that is an optically active 4-halogeno-1,3-butanediol [1], an optically active 1,2,4-butanetriol [2] and an optically active 3-hydroxy-γ-butyrolactone [3] in highly optical purity, which are very important as intermediates in making pharmaceuticals, agrochemicals or physiologically active compounds.

Racemate[1] which is used as the starting material in the present invention, can be easily obtained by reducing a racemic 4-halogeno-3-hydroxybutanoic acid ester such as racemic 4-chloro-3-hydroxybutanoic acid methyl ester with sodium boron hydrate or lithium aluminum hydride etc. [Comprehensive Organic Transformation, pp. 548–552 (1989). by Richard C. Larock, VCH Publishers, Inc.; J. Am. Chem. Soc., 158–163(1950); Tetrahedron Lett., 2709–2712 (1987); Tetrahedron Lett., 6069–6072 (1987).

The present invention is in detail explained below.

In order to obtain (S)-form[1] and (R)-form[2], or (R)-form[1] and (S)-form[3] from racemate[1] as a substrate, a microorganism belonging to the genus Pseudomonas having stereoselective dehalogenating activity, namely Psedomonas sp. DS-K-436-1, or Psedomonas sp. DS-SI-5 is cultivated and thereto a substrate, racemate[1] is added to react the microorganism.

The reaction is preferably carried out within optimum pH of the strain used herein and optimum temperature.

When pH gradually becomes lower by halogen ion released from the substrate[1] with progress of the reaction, it is necessary to adjust pH of the reaction solution to optimum pH by addition of an alkali. The solution is preferably controlled in the range of optimum pH by using an acid-neutralizing agent, such as an aqueous alkali carbonate solution, e.g. an aqueous calcium carbonate solution, an aqueous sodium carbonate solution, an aqueous potassium carbonate solution or an aqueous ammonium carbonate solution, an aqueous alkali hydroxide solution, e.g. sodium hydroxide solution, an aqueous potassium hydroxide solution or an aqueous calcium hydroxide solution, or an aqueous ammonium solution.

Illustratively, the reaction is conducted by keeping pH at 6–8, the temperature at 15–50° C., preferably 25–35° C. The concentration of the substrate in the raction is preferably 0.1–15%(w/w). The reaction is efficiently conducted under stirring or agitating.

The culture medium for cultivation of the microorganism related to the present invention is not limited as long as the microorganism can grow in the culture medium. For example, there are illustrated carbohydrates such as glucose, galactose, fructose or sucrose, alcohols such as glycerol, a racemic 3-halogeno-1,2-propanediol or a racemic 2,3-dichloro-1-propanol, organic acids, such as acetic acid, citric acid, malic acid, maleic acid, fumaric acid or gluconic acid, or a salt thereof, or a mixture thereof, as carbon source, and inorganic nitrogen compounds such as ammonium sulfate, ammonium nitrate or ammonium phosphate, organic nitrogen compounds such as urea, peptone, casein, yeast extract, meat extract, corn steep liquor or a mixture thereof as nitrogen source. Further, inorganic salts such as a phosphoric acid salt, a magnesium salt, a potassium salt, a manganese salt, an iron salt, a zinc salt, a cooper salt, or if suitable, vitamins may be used.

As enzyme-inducing additives to obtain the microorganism having high enzyme activity, to the above mentioned culture medium, nutrient medium such as peptone medium or bouillon medium may be added a racemic 3-halogeno-1,2-propanediol or racemic 2,3-dichloro-1-propanol. Furthermore, there is effectively cultured in the synthesized medium containing a racemic 3-halogeno-1,2-propanediol, or racemic 2,3-dichloro-1-propanol as a single-carbon source.

The microorganismus related to the present invention can be cultivated as in the usual manner, for example at pH 4–10, preferably 5–9, at the temperature 15–50° C., preferably 20–37° C., and aerobically for 10–96 hours.

(1) The culture broth prepared by the above cultivation,
(2) the cells prepared by centrifugation of the culture broth (1), or its treated cells (disrupted cells or cell-free extracts),
(3) a mixture of the product prepared by the immobilization of the cells et al. of above (1) or (2), by the usual method, with a buffer solution etc., or
(4) an enzyme(s) extracted from the above cells can be reacted with the substrate[1] to obtain the object compound(s), too.

The above reaction is carried out preferably at 15–50° C. and preferably at pH 6–8. The concentration of the substrate in the reaction mixture is preferably 0.1–15%(v/v) and the substrate may be added at once in the initial stage or in several times.

The reaction is usually carried out under shaking or agitation, and the reaction is preferably completed in 1– 120 hours, depending on the concentration of the substrate or amount of the microorganism. When the residual amount of the racemic substrate[1] becomes 50% comparing with the initial concentration of the substrate[1] by gas chromatography, the reaction is preferably quenched, or with measurement of optical purity on the optically active compound, preferably with subjecting to gas chromatography, the end point may be preferably determined.

Thus obtained optically active compounds[1] and [2], or [3] remaining in the reaction solution are recovered, separated and purified by the conventional method. For example, after removal of cells from the reaction medium by centrifugation, the supernatants are condensed with an evaporator, extracted with a solvent such as ethyl acetate or ethanol, etc. The extract is dried over anhydrous magnesium sulfate, and then the solvent is evaporated in vacuo to obtain a mixture of an optically active compound [1] and an optically active compound [2] or an optically active compound [3] in syrup. Additionally, the purification by distillation may be carried out.

In order to separate an optically active compound [1], an optically active compound [2], or an optically active compound [3], 1) the reduced distillation method by utilizing the difference of boiling points,
2) many kinds of chromatography by using a separation material such as silica gel, active carbon, ion exchange, etc., or
3) the solvent-extraction method by using the difference of distribution ratio, is carried out.

The conversion method of an optically active compound [1] into an optically active compound [2] or an optically active compound [3] by reacting the optically active compound[1] with a microorganism belonging to the genus Pseudomonas, such as Pseudomonas sp. OS-K-29, Pseudomonas sp. 436-1, or Pseudomonas sp. DS-SI-5, or a culture broth thereof or an enzyme(s) derived from said strain is also carried out in the same manner as mentioned above. This reaction mildly proceeds, the optical purity does not decrease and therefore, this reaction method is very important and beneficial.

Pseudomonas sp. OS-K-29 was already deposited with the National Institute of Bioscience and Human-Technology Agency of Industrial Science and Technology, of 1–3, Higashi 1-chome, Tsukuba-shi, Ibaraki-ken, 305–8566 Japan on September 14, 1984 under the Budapest Treaty with an accession number of FERM BP-994. Other two strains are newly named as DS-K-436-1 and DS-SI-5, respectively and identified to strains belonging to species of the genus Pseudomonas from their physiological and bacteriological properties. These new strains have been deposited with the National Institute of Bioscience and Human-Technology Agency of Industrial Science and Technology, of 1–3, Higashi 1-chome, Tsukuba-shi, Ibaraki-ken, 305–8566 Japan on Oct. 7, 1999 and Oct. 7, 1999, respectively, under the Budapest Treaty with an accession number of FERM BP-7079 and FERM BP-7080, respectively.

Physiological and bacteriological properties on new strains of Pseudomonas (DS-K-436-1 strain, and DS-SI-5 strain) are shown below.

Growth in Various Media

1. Bouillon-agar Plate Medium (30° C., cultivation for 3 Days)

| Strains | DS-K-4361-1 | DS-SI-5 |
| --- | --- | --- |
| a) Speed of colony growth: | ordinary | ordinary |
| b) Shape of colonies: | circular | circular |
| c) Shape of colony surface: | smooth | smooth |
| d) Raised condition of colonies: | caput | convex |
| e) Periphery of colonies: | entire | undulate |
| f) Contents of colonies: | homogeneous | homogeneous |
| g) Color of colonies: | white | pale brown |
| h) Transparency of colonies: | none | none |
| i) Gloss of colonies: | yes | none |
| j) Formation of soluble pigment: | none | none |

2. Bouillon-agar Slant Medium (30° C., cultivation for 3 Days)

| Strains | DS-K-436-1 | DS-SI-5 |
| --- | --- | --- |
| a) Growth degree: | good | good |
| b) Growth condition: | expansive | expansive |
| c) Shape of colony surface: | smooth | smooth |
| d) Shape of colony in section: | flat | flat |
| e) Gloss of colonies: | yes | yes |
| f) Color of colonies: | white | pale brown |
| g) Transparency of colonies: | none | none |

3. Bouillon-liquid Medium (30° C., Cultivation for 3 Days)

| Strains | DS-K-436-1 | DS-SI-5 |
| --- | --- | --- |
| a) Growth degree: | good | good |
| b) Generation of gas: | none | none |
| c) Coloring of medium: | none | none |
| d) Status | precipitation | precipitation |

4. Bouillon-agar Stuck Medium (30° C., Cultivation for 3 Days)

| Strains | DS-K-436-1 | DS-SI-5 |
| --- | --- | --- |
| a) Growth place: | surface | surface |
| b) Growth degree of surface: | good | good |
| 5. Bouillon-gelatin stuck medium | not liquefied | not liquefied |

6. Physiological Properties

| Strains | | DS-K-436-1 | DS-SI-5 |
| --- | --- | --- | --- |
| 1) | Reduction on nitrate | − | + |
| 2) | V-P test | − | − |
| 3) | MR test | − | − |
| 4) | Production of indole | − | − |
| 5) | PPA | − | − |
| 6) | Production of $H_2S$ | − | − |
| 7) | Decarboxylation of lysine | + | + |
| 8) | Utilization of citric acid | ± | + |
| 9) | Hydrolysis of starch | − | − |
| 10) | Catalase | + | + |
| 11) | Urease | + | + |
| 12) | Oxidase | + | + |
| 13) | Denitrification | − | + |
| 14) | Production of fluorescent pigment | | |
| | King's A | − | − |
| | King's B | − | − |
| | Pseudomonas F | − | − |
| | Pseudomonas P | − | − |
| 15) | Litmus milk | | |
| | Agglutination | − | − |

-continued

| Strains | | DS-K-436-1 | DS-SI-5 |
|---|---|---|---|
| | Reduction | − | − |
| 16) | Accumulation of PHB | + | + |
| 17) | O-F test | | |
| | D-Glucose | 0 | 0 |
| | D-Galactose | 0 | 0 |
| | Fructose | 0 | 0 |
| | Lactose | 0 | — |
| | Glycerin | 0 | 0 |
| | Mannitol | 0 | — |
| | Sucrose | 0 | — |
| 18) | Utilization of carbon sorce | | |
| | D-Glucose | + | + |
| | D-Galactose | + | − |
| | Fructose | + | + |
| | Trehalose | + | − |
| | Glycerin | + | − |
| | Mannitol | + | − |
| | Sucrose | + | − |
| | p-Hydroxybenzoate | + | + |

7. Morphological Properties

| | Strains | DS-K-436-1 | DS-SI-5 |
|---|---|---|---|
| 1) | Shape of cells | rods | rods |
| 2) | Size of cells (μm) | 1.1–1.4 | 1.3–1.6 |
| 3) | Width of cells (μm) | 0.4–0.6 | 0.4–0.6 |
| 4) | Pleomorphisms of cell | none | none |
| 5) | Flagella | multi polar | single polar |
| 6) | Mobility | + | + |
| 7) | Gram stain | — | — |
| 8) | Spores | — | — |
| 9) | Acid fastness | — | — |
| 10) | Capsules | none | none |

The present invention is illustratively explained by following examples, but should not be limited by these examples. Percentage(%) in examples means %(w/v), if not defined otherwise.

EXAMPLE 1

A nutrient medium (100 ml, pH 7.2) consisting of polypeptone (1.0%), yeast extract (1.0%) and glycerin (1.0%) were poured into an Erlenmeyer flask (500 ml) with a baffle and the flask was sterilized at 121° C. for 15 minuets. Previously, Pseudomonas sp. DS-K-436-1 were made stationary incubation in the agar medium (pH 7.2) containing polypeptone (1.0%), yeast extract (1.0%) and glycerin (1.0%) at 30° C. for 24 hours to prepare seed strains and a loopful of the strains was seeded to the above medium. The culture medium was cultivated with agitation (125 rpm) at 30° C. for 24 hours. After the cultivation, the culture broth was taken out, the cells were collected by centrifugation and washed three times by phosphate buffer (20 m M, pH 7.2) containing magnesium sulfate (2 mM) to prepare resting cells. The cells were suspended in the phosphate buffer containing 1.0% of calcium carbonate in an Erlenmeyer flask (500 ml) equipped with a baffle. To the suspension was added 1 ml of racemic 4-chloro-1,3-butanediol and the mixture was reacted at 30° C. under stirring. At that time the remaining amount of racemic 4-chloro-1,3-butanediol was measured with gas chromatography (column support: PEG20M, 60–80 mesh) to be 35% in the remaining ratio. After the reaction, the reaction mixture was concentrated to about 1 ml and extracted with ethanol. The extract was dried over magnesium sulfate and the solvent was removed in vacuo to give 368 mg of 4-chloro-1,3-butanediol and 590 mg of 1,2,4-butanetriol. The identification and determination of these compounds was made by subjecting to the above gas chromatography and GC-MS.

The measurement of optical isomers of 4-chloro-1,3-butanediol in the syrup thus obtained was carried out by subjecting to gas chromatography with Capillary column: astec CHIRALDEX G-TA (inner diameter; 0.25 mm×30 m). On the other hand, in regard to 1,2,4-butanetriol, after it was trifluoacetylated with trifluoroacetic acid anhydride, the measurement of optical isomers of it was carried out by subjecting to the above gas chromatography.

As results, 4-chloro-1,3-butanediol recovered was 99.5% ee in the optical purity and was (S)-form, and 1,2,4-butanetriol recovered was 52% ee in the optical purity and was (R)-form.

Conditions on the above gas chromatography analysis were as follows:

(1) Retention time of 4-chloro-1,3-butanediol: (R)-form, 15.9 min.; (S)-form, 17.1 min.

Analysis temperature: Column temp. (120° C.), Inject temp.: 200° C.

Carrier gas: nitrogen (flow 0.5 ml/min.), Split ratio: 200/1, Detection: FID 200° C.

(2) Retention time of trifluoroacetylated 1,2,4-butanetriol: (R)-form, 39.8 min.; (S)-form, 40.4 min. Analysis temperature: Column temp. (100° C.), Inject temp. 200° C.

Carrier gas: nitrogen (flow 0.5 ml/min.), Split ratio: 200/1, Detection: FID 200° C.

EXAMPLE 2

In the same manner as above Example 1, by using Pseudomonas sp. DS-SI-5 instead of Pseudomonas sp. DS-K-436-1 there are obtained 399mg of 4-chloro-1,3-butanediol and 579 mg of 3-hydroxy-γ-butyrolactone (extract solvent: ethyl acetate).

The identification and determination of these compounds was made by subjecting to the above gas chromatography and GC-MS.

The measurement of optical isomers of 4-chloro-1,3-butanediol in the syrup thus obtained was carried out by subjecting to gas chromatography with Capillary column: astec CHIRALDEX G-TA (inner diameter; 0.25 mm×30 m). On the other hand, in regard to 3-hydroxy-γ-butyrolactone, after it was trifluoroacetylated with trifluoroacetic acid anhydride, the measurement of optical isomers of it was carried out by subjecting to the above gas chromatography.

As results, 4-chloro-1,3-butanediol recovered was 99% ee in the optical purity and was (R)-form, and 3-hydroxy-γ-butyrolactone recovered was 58% ee in the optical purity and was (S)-form.

EXAMPLES 3–8

The following Examples ware carried out in the same manner as the above Example 1 except for the microorganism and the substrate. In Examples 7 and 8, as the extract solvent ethyl acetate was used.

The identification and determination of these compounds and the measurement of optical isomers of these compounds were carried out in the same method as the above Example 1. The measurement of the optical purity of 3-hydroxy-γ-butylolactone obtained in Examples 7 and 8 was carried out in the same conditions as Example 1 after trifluoroacetylization of it.

The results were shown in the following Table.

| Example | Strain (Pseudomonas sp.) | Substrate | Product | Production rate (mg) |
|---|---|---|---|---|
| 3 | DS-K-436-1 | (R)CBD(99% ee) | (R)BT(99% ee) | 850 |
| 4 | DS-K-436-1 | (S)CBD(99% ee) | (S)BT(99% ee) | 842 |
| 5 | OS-K-29 | (R)CBD(99% ee) | (R)BT(99% ee) | 873 |
| 6 | OS-K-29 | (S)CBD(99% ee) | (S)BT(99% ee) | 860 |
| 7 | DS-SI-5 | (R)CBD(99% ee) | (R)HL(99% ee) | 840 |
| 8 | DS-SI-5 | (S)CBD(99% ee) | (S)HL(99% ee) | 835 |

In the above Table the abreviations mean as follows:
CBD; 4-Chloro-1,3-butanediol
BT; 1,2,4-Butanetriol
HL; 3-Hydroxy-γ-butyrolactone

EFFECT OF THE INVENTION

According to the process of the present invention, (S)-form[1] and (R)-form[2], or (R)-form[1] and (S)-form[3] are conveniently and economically obtained from a racemic compound[1] by using Pseudomonas sp. DS-K-436-1 or Pseudomonas sp. DS-SI-5. In addition, by using a microorganism belonging to the genus Pseudomonas the conversion of an optically active compound[1] into an optically active compound[2] or [3] without decrease of optical purity can be industrially and conveniently performed.

What is claimed is:

1. A process for preparing an optically active 4-halogeno-1,3-butanediol represented by the following formula[1]

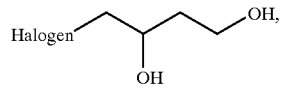

which comprises reacting aracemic 4-halogeno- 1,3-butanediol[ 1] with Pseudomonas sp. DS-K-436-1 (FERM BP-7079) or Pseudomonas sp. DS-SI-5 (FERM BP-7080), its culture broth or an enzyme(s) derived from said strain, and then isolating the optically active 4-halogeno-1,3-butanediol[1].

2. A process for preparing a (S)-4-halogeno-1,3-butanediol[1] and (R)-1,2,4-butanetriol represented by the following formula[2]

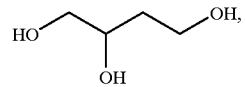

which comprises reacting a racemic4-halogeno-1,3-butanediol[1] with Pseudomonas sp. DS-K-436-1, its culture broth or an enzyme(s) derived from said strain, and isolating the (S)-4-halogeno-1,3-butanediol[1] and (R)-1,2,4-butanetriol[2].

3. A process for isolating (R)-1,2,4-butanetriol[2], which comprises reacting a racemic 4-halogeno-1,3-butanediol[1] with Pseudomonas sp. DS-K-436-1, its culture broth or an enzyme(s) derived from said strain and then isolating the (R)-1,2,4-butanetriol[2].

4. A process for preparing a (R)-4-halogeno-1,3-butanediol[1] and (S)-3-hydroxy-γ-butyrolactone represented by the following formula[3]

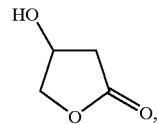

which comprises reacting a racemic 4-halogeno-1,3-butanediol[1] with Pseudomonas sp. DS-SI-5, its culture broth or an enzyme(s) derived from said strain, and isolating the (R)-4-halogeno-1,3-butanediol[1] and (S)-3-hydroxy-y-butyrolactone[3].

5. A process for isolating (S)-3-hydroxy-γ-butyrolactone [3], which comprises reacting a racemic 4-halogeno-1,3-butanediol[1] with Pseudomonas sp. DS-SI-5, its culture broth or an enzyme(s) derived from said strain, and then isolating the (S)-3-hydroxy-y-butyrolactone[3].

6. A process for preparing an optically active 1,2,4-butanetriol[2] or an optically active 3-hydroxy-γ-butyrolactone[3], which comprises reacting an optically active 4-halogeno-1,3-butanediol[1] with a microorganism belonging to the genus Pseudomonas, its culture broth or an enzyme(s) derived from said strain, and isolating the optically active 1,2,4-butanetriol[2] or optically active 3-hydroxy-γ-butyrolactone[3].

7. A process for isolating an optically active 1,2,4-butanetriol[2], which comprises reacting an optically active 4-halogeno-1,3-butanediol[1] with Pseudomonas sp. DS-K-436-1, or Pseudomonas sp. OS-K-29, its culture broth or an enzyme(s) derived from said strain, and then isolating the optically active 1,2,4-butanetriol[2].

8. A process for isolating an optically active 3-hydroxy-γ-butyrolactone[3], which comprises reacting an optically active 4-halogeno-1 ,3-butanediol[1] with Pseudomonas sp. DS-SI-5, or, its culture broth or an enzyme(s) derived from said strain, and then isolating the optically active 3-hydroxy-γ-butyrolactone[3].

9. The process for isolating (R)-1,2,4-butanetriol[2] of claim 7, which comprises reacting a (R)-4-halogeno-1,3-butanediol[1] with Pseudomonas sp. DS-K-436-1, or Pseudomonas sp. OS-K-29 (FERM BP-994), its culture broth or an enzyme(s) derived from said strain.

10. The process for isolating (S)-1,2,4-butanetriol[2] of claim 7, which comprises reacting a (S)-4-halogeno-1,3- butanediol[1] with Pseudomonas sp. DS-K-436-1, or Pseudomonas sp. OS-K-29, its culture broth or an enzyme(s) derived from said strain.

11. The process for isolating (R)-3-hydroxy-γ-butyrolactone[3] of claim 8, which comprises reacting a (R)-4-halogeno-1,3-butanediol[1] with Pseudomonas sp. DS-SI-5, its culture broth or an enzyme(s) derived from said strain.

12. The process for isolating (S)-3-hydroxy-γ-butyrolactone[3] of claim 8, which comprises reacting a (R)-4-halogeno-1,3-butanediol[1] with Pseudomonas sp. DS-SI-5, its culture broth or an enzyme(s) derived from said strain.

* * * * *